United States Patent

Guit et al.

[11] Patent Number: 5,973,143
[45] Date of Patent: *Oct. 26, 1999

[54] PROCESS TO PREPARE $\epsilon$-CAPROLACTAM FROM 6-AMINOCAPROIC ACID

[75] Inventors: Rudolf P. M. Guit, Maastricht, Netherlands; Samuel L. Lane, Beaumont, Tex.; Wim Buijs, Schinnen, Netherlands

[73] Assignee: DSM N.V., Herleen, Netherlands

[*] Notice: This patent is subject to a terminal disclaimer.

[21] Appl. No.: 09/141,406

[22] Filed: Aug. 21, 1998

Related U.S. Application Data

[63] Continuation of application No. PCT/NL97/00056, Feb. 12, 1997, and a continuation of application No. 08/605,883, Feb. 23, 1996, Pat. No. 5,780,623.

[51] Int. Cl.$^6$ .................................................. C07D 201/08
[52] U.S. Cl. ............................................................. 540/538
[58] Field of Search ............................................... 540/538

[56] References Cited

U.S. PATENT DOCUMENTS

| | | | |
|---|---|---|---|
| 3,485,821 | 12/1969 | Sheehan | 260/239.3 |
| 3,988,319 | 10/1976 | Mares | 260/239.3 |
| 4,599,199 | 7/1986 | Fuchs | 260/239.3 |
| 4,730,040 | 3/1988 | Vagt | 540/538 |
| 4,730,041 | 3/1988 | Hutmacher et al. | 540/538 |
| 4,767,856 | 8/1988 | Dockner | 540/538 |
| 4,767,857 | 8/1988 | Merger | 540/538 |
| 4,963,673 | 10/1990 | Merger et al. | 540/538 |
| 5,502,185 | 3/1996 | Eberhard | 540/538 |
| 5,700,934 | 12/1997 | Wolters et al. | 540/538 |
| 5,717,089 | 2/1998 | Wolters et al. | 540/538 |
| 5,780,623 | 7/1998 | Guit et al. | 540/538 |

FOREIGN PATENT DOCUMENTS

| | | |
|---|---|---|
| 0 242 505 | 10/1987 | European Pat. Off. . |
| 47 010 715 | 5/1972 | Japan . |
| 95 19950 | 7/1995 | WIPO . |

OTHER PUBLICATIONS

Mares et al., *Kinetics of Caprolactam Formation From 6-Aminocaproic Acid, Ester, and Amide, Ind.* Eng. Chem. Process Des. Dev., 1978, vol. 17, No. 1, pp. 9–16.

*Primary Examiner*—Mukund J. Shah
*Assistant Examiner*—Bruck Kifle
*Attorney, Agent, or Firm*—Pillsbury Madison & Sutro LLP

[57] ABSTRACT

Process to prepare $\epsilon$-caprolactam starting from a liquid aqueous mixture containing an alcohol and 6-aminocaproic acid by cyclization of 6-aminocaproic acid in the aqueous mixture at an elevated temperature. The alcohol is separated from the starting aqueous mixture before performing the cyclization to such extent that the concentration of alcohol in the aqueous mixture during the cyclization is less than 1 wt. %. The advantages include reduced amounts of undesirable by-product.

3 Claims, No Drawings

PROCESS TO PREPARE ε-CAPROLACTAM FROM 6-AMINOCAPROIC ACID

This is a Continuation of International Appln. No. PCT/NL97/00056 filed Feb. 12, 1997 which designated the U.S., and a continuation of application Ser. No. 08/605,883 filed Feb. 23, 1996 now U.S. Pat. No. 5,780,623.

The invention relates to a process to prepare ε-caprolactam starting from a liquid aqueous mixture containing a $C_1$–$C_6$ alcohol and 6-aminocaproic acid by cyclization of 6-aminocaproic acid in the aqueous mixture at an elevated temperature.

Such a process is described in U.S. Pat. No. 4,730,040. This patent publication describes a process in which first methyl 5-formylvalerate is hydrolysed in an aqueous medium to methanol and 5-formylvaleric acid. In a second step, the aqueous mixture obtained in the first step is contacted with ammonia and hydrogen in the presence of a hydrogenation catalyst. In this step 6-aminocaproic acid and a small amount of ε-caprolactam is obtained. The resulting aqueous mixture, which mixture will contain the methanol formed in the first step, is heated to a temperature between 150 and 370° C. at which temperature 6-aminocaproic acid reacts by cyclization to ε-caprolactam.

A disadvantage of this process is that the resulting ε-caprolactam contains an undesirable amount of N-methyl caprolactam. It has been found that these by-products and its precursors, N-methyl 6-aminocaproic acid and N-methyl 6-aminocaproic acid amide, are especially formed when performing the cyclization reaction at the elevated temperatures. The presence of these N-substituted caprolactam by-products has a negative influence on the ε-caprolactam yield and makes the resulting ε-caprolactam less suitable to be used as commercial starting material for, for example, Nylon-6 fibers. Furthermore, it is not easy to remove these N-substituted caprolactam by-products from ε-caprolactam.

The object of this invention is a process in which the amount of N-substituted caprolactam by-products in the resulting ε-caprolactam after cyclization are not or are practically not present.

This object is achieved in that the alcohol is separated from the starting aqueous mixture before performing the cyclization to such extent that the concentration of alcohol in the aqueous mixture during the cyclization is less than 1 wt %. Preferably, the concentration of alcohol is less than about 0.1 wt. %.

It has been found that by performing the cyclization step when practically no alcohol is present, the amount of N-substituted caprolactam in the ε-caprolactam product is substantially less than when the state of the art process is used.

It was not to be expected that the presence of an alcohol during the cyclization reaction of 6-aminocaproic acid would have such a disadvantageous effect on ε-caprolactam yield and quality. No mention of this fact is found in the earlier mentioned U.S. Pat. No. 4,730,040. Furthermore, comparable yields to ε-caprolactam starting from 6-aminocaproic acid were found in a pure alcohol solvent and a pure water solvent in an in depth study by Mares F. and Sheehan D., described in Ind. Eng. Chem. Process Des. Dev., Vol. 17, no. 1, 1978 pages 9–16. Furthermore, no mention of the N-substituted by-products were found in this article.

The aqueous starting mixture of the process according to the invention may be obtained as the reaction product of the reductive amination of 5-formylvaleric acid or the corresponding ester or, for example, as the reaction product of the reduction of 5-cyanovaleric acid or the corresponding ester. These ester compounds can be readily converted to acid compounds by simple hydrolysis processes yielding the corresponding acid and an alcohol. For example, when the reductive amination or reduction is performed in water, this hydrolysis may take place simultaneously. The aqueous starting mixture obtained, for example, via reductive amination will generally comprise in addition to the alcohol also some ammonia.

Aqueous mixtures which are advantageously used in the present invention are aqueous mixtures obtained by reacting an $C_1$–$C_6$ alkyl 5-formylvalerate with ammonia and hydorgen in the presence of a hydrogenation catalyst in a water solvent. By using water as solvent in this reaction the ester group of the 5-formylvalerate will hydrolyze in the same process step as in which the aldehyde group reacts to the amine group (reductive amination). Alcohol will be formed in the hydrolysis reaction and will thus be present in the resulting aqueous mixture next to optionally 6-aminocaproic acid, 6-aminocaproamide, ε-caprolactam, some non-hydrolyzed $C_1$–$C_6$ alkyl 6-aminocaporate and oligomers of 6-aminocaproic acid and/or 6-aminocaproamide.

The combined hydrolysis/reductive amination may be performed at a temperature of between 40–200° C., and preferably between 80–160° C. The molar ratio between $C_1$–$C_6$ alkyl 5-formylvalerate is preferably between 3:1 and 30:1. The pressure is preferably between 0.5 and 10 MPa. The amount of hydrogen is at least equal to the molar quantity of the $C_1$–$C_6$ alkyl 5-formylvalerate.

Preferably 1–15 wt. % alcohol is present in he aqueous mixture next to the $C_1$–$C_6$ alkyl 5-formylvalerate. The alcohol is preferably the corresponding alcohol of the $C_1$–$C_6$ alkyl ester group. The additional alcohol improves the solubility of the $C_1$–$C_6$ alkyl 5-formylvalerate in water.

The hydrogenation catalyst is preferably a supported or non-supported catalyst comprising a metal from Group VIII of the Periodic Table of elements, for example nickel, cobalt, ruthenium, plantinum, palladium and iridium. Preferably nickel, cobalt or ruthenium is used. More preferably a ruthenium comprising catalyst is used.

The $C_1$–$C_6$ alkyl group may be for example methyl, ethyl, propyl, iso-propyl, n-butyl, tert-butyl, iso-butyl, pentyl or cyclohexyl. Preferably methyl and ethyl groups are used.

Below, the composition of the aqueous mixture after separating the alcohol, is given, which mixture may be used as feed or starting mixture for the cyclization. The concentration of 6-aminocaproic acid in the mixture is generally between 2 and 40 wt. % and preferably between 5–30 wt. %. The aqueous mixture can also contain between 0 and 20 wt. % 6-aminocaproamide and between 0 and 2 wt. % 6-aminocaproate ester, between 0–15 wt. % ε-caprolactam, and between 0 and 10 wt. % oligomers of 6-aminocaproic acid and/or 6-aminocaproamide. These compounds can also advantageously be reacted to ε-caprolactam by cyclization under the same reaction conditions as are valid for 6-aminocaproic acid. If these compounds are also present, the concentration of 6-aminocaproic acid is preferably between 2–20 wt. %.

More preferably, the aqueous mixture comprises between 2–20 wt. % 6-aminocaproamide, between 2–15 wt. % ε-caprolactam, between 2–15 wt. % 6-aminocaproic acid, between 1–8 wt. % oligomers, and between 60–90 wt. % water.

The total concentration of 6-aminocaproic acid, ε-caprolactam, 6-aminocaproamide, 6-aminocaproate and oligomers, if present, during cyclization is preferably between about 5 and about 50 wt. %, and more preferably between about 10 and about 35 wt. %. Most preferably, the concentration is above about 15 wt. %. Higher concentration levels are advantageous because smaller process equipment can be used.

The alcohol to be separated is generally a $C_1$–$C_6$ alkanol such as, for example, methanol, ethanol, propanol, butanol, pentanol or hexanol, or as an aromatic alcohol, for example, phenol. When 6-aminocaproic acid is obtained starting from a 5-formylvalerate ester or 5-cyanovalerate ester, the alcohol is generally the alcohol which corresponds with the ester group of these esters. Generally, these corresponding alcohols are methanol and ethanol.

The starting aqueous mixture comprises at least about 1 wt. % of alcohol.

Separating the alcohol may be performed by any known method known to the man skilled in the art, for example, distillation or stripping, for example, steam stripping.

Preferably, the alcohol is removed by stripping the aqueous mixture with steam. In a commercial large scale process, the stripping preferably involves the continuous counter current contacting of the aqueous starting mixture with upflowing steam in a vertical positioned column, in which at the top a water/alcohol stream and at the bottom an alcohol-poor aqueous product stream is obtained. Steam stripping is advantageous because the alcohols can be removed very effectively and because a convenient concentration of the ε-caprolactam precursors and ε-caprolactam in resulting aqueous mixture can be obtained such that the aqueous mixture can be directly used in the cyclization. In this process, ammonia is also removed to a large extent.

The steam stripping is generally performed at a pressure between about ambient pressure and about 1.0 MPa, and more preferably, at near atmospheric conditions. The pressure is not very critical, but near atmospheric conditions are preferred because less expensive process equipment is required and the steam stripping is more effective at this pressure.

The temperature for cyclization is generally between about 200 and about 350° C. Preferably, the temperature is between about 270 and about 330° C. More preferably, the temperature is higher than 280° C., because higher selectivities to ε-caprolactam and thus a higher overall yield to ε-caprolactam is obtained.

The pressure for cyclization is preferably between about 5.0 and about 20 Mpa. Normally, this pressure will be greater than or equal to the resulting pressure of the liquid reaction mixture and the temperature employed. The pressure is so chosen that the resulting product stream is obtained as a liquid.

Preferably, the process according to the invention is performed continuously.

The cyclization can be performed continuously in process equipment resulting in high and low rates of backmixing, for example, in a (or optionally a series of) well mixed tank reactor(s) or a tube reactor.

Preferably, the following steps are performed continuously:

a) separating the alcohol from the aqueous starting mixture;
b) feeding the resulting aqueous mixture to a reaction zone in which the cyclization is performed;
c) separating ε-caprolactam from the aqueous mixture leaving the reaction zone; and
d) recycling the mixture poor in ε-caprolactam obtained in step c), comprising unconverted 6-aminocaproic acid and oligomers, to the reaction zone.

The mixture poor in ε-caprolactam obtained in step c) may also contain 6-aminocaproamide and/or ε-caprolactam.

The ε-caprolactam can be separated from the reaction mixture obtained by cyclization by, for example, crystallization, extraction or by distillation. Examples of possible extraction agents are methylene chloride, cyclohexane, toluene, benzene, chloroform or trichloroethene.

Preferably, not all of the ε-caprolactam is separated from the mixture obtained by the cyclization if the ε-caprolactam is separated by distillation. It has been found that the oligomers are more easily handled when the distillation residue is mixed with some ε-caprolactam. Preferably between 5 and 50 wt. % ε-caprolactam is present in the residue. By performing the process according to the invention, it has been found that almost no build-up of oligomers in the circulating mixture takes place and that the overall yield to ε-caprolactam of practically 100% is possible based on the 6-aminocaproic acid, 6-aminocaproamide, $C_1$–$C_6$ alkyl 6-aminocaproate and oligomers which may be present in the aqueous starting mixture.

The invention will be elucidated with the following non-restricting examples. In these examples, "mol olig" means the equivalent amount in mol ε-caprolactam which potentially can be formed by that amount of oligomers. For example, one actual mol of dimer is equal to two mol oligomer because the dimer can yield potentially two mol of ε-caprolactam. The following abbreviations will be used: 6ACA=6-aminocaproic acid; 6ACAM=6-aminocaproamide; M6AC=methyl 6-aminocaproate; 6-N-Me ACA=6 N-methyl aminocaproic acid; and 6-N-Me ACAM=6 N-methyl aminocaproamide.

EXAMPLE I 40 grams of 5 wt % ruthenium on alumina were introduced in a 1 liter Hastelloy-C reactor. After the addition of water, the catalyst was prereduced at 140° C. during 12 hours. Subsequently, an aqueous stream of 775 grams per hour, consisting of 25 wt. % methyl-5-formylvalerate, 30 wt. % ammonia and 7 wt. % methanol in water, was fed continuously to the reactor. The reactor was kept at a constant pressure of 3.0 MPa by a hydrogen stream of 10 grams per hour. The reaction was performed at 120° C. A yield of 97% to ε-caprolactam, 6-aminocaproic acid, 6-aminocaproamide and oligomers (desired products), was obtained.

EXAMPLE II 50 grams of Raney-Nickel were introduced in a 1 liter Hastelloy-C reactor. An aqueous stream of 847 grams per hour, consisting of 5 wt. % methyl-5-formylvalerate and 20 wt. % ammonia in water, was fed continuously to the reactor. The reactor was kept at a constant pressure of 1.5 MPa by a hydrogen stream of 10 grams per hour. The reaction was performed at 100° C.

The yield of desired products was 96%.

Examples I and II illustrate a combined hydrolysis/reductive amination of methyl-5-formylvalerate in which an aqueous mixture is obtained comprising methanol and 6-aminocaproic acid (and other precursors to ε-caprolactam).

EXAMPLE III

Methanol and ammonia were separated from a feed consisting of 5 wt. % CAP, 20.8 wt. % 6ACA, 10.0 wt. % $NH_3$, 0.03 wt. % oligomers, 0.1 wt. % 6 ACAM, 9.1 wt. % methanol and 55 wt. % water by feeding an Oldershaw sieve tray column (6 cm diameter and 20 trays) at atmospheric pressure at a rate of 1820 g/hr. The reboiler in which stream was generated operated on the thermosiphoning principle. The overhead vapor was passed through two condensers arranged in series; the first was operated with cooling water (18° C.) and the second with a coolant at 0° C. for effective condensation of methanol. 1036 g/hr of water was added to the reboiler in order to dilute the bottoms. The methanol concentration in the bottom stream was analyzed and contained 40 ppm methanol. The bottom stream had a rate of 2475 g/hr of which 80 wt. % $H_2O$. No CAP, 6ACA, oligomer and 6 ACAM was found in the top stream. No ammonia was analyzed in the bottoms. The bottom temperature was 100° C. and the top temperature was 70° C.

EXAMPLE IV

A mixture consisting of 4.8 wt. % $NH_3$, 6.5 wt. % methanol, 66.0 wt. % $H_2O$ and 21.7 wt. % of ε-caprolactam precursors of which 19.6 mol % 6ACA, 36.9 mol % 6 ACAM, 31.5 mol % CAP, 2.4 mol % methyl 6-aminocaproate and 9.6 mol % oligomers was continuously fed for 22 hours to the top of a steamstripper column at a rate of approximately 550 gr/hr. Steam was generated in a reboiler of the column. To the column also 350 gr/hr of fresh water was fed. In the steamstripper column the liquid product stream was thus contacted with an upflowing stream of steam. The bottom temperature in the column was kept at 100° C. The liquid bottom stream which left the steamstripper at a rate of 742 gr/hr did not contain any detectable amount of methanol and $NH_3$. The concentration of ε-caprolactam and ε-caprolactam precursors in the liquid bottom stream was 22.1 wt. % in water (1.33 mol/hr). After 22 hours, 16.3 kg of this mixture was collected containing a total of 29.26 mol of ε-caprolactam and ε-caprolactam precursors (3.3 wt. % 6ACA, 9.3 wt. % 6ACAM, 6.9 wt. % ε-caprolactam and 2.6 wt. % oligomers).

This liquid mixture was fed continuously to a plugflow cyclization reactor at a rate of approximately 500 gr/hr and a temperature of 300° C. The cyclization was carried out at 300° C., with almost no back mixing, 10 Mpa and at a residence time of approximately 30 minutes. Temperature was held essentially constant with use of an oil bath. After cooling and depressurizing, the average composition of all the products present in the liquid aqueous stream amounted to 70.5 mol % ε-caprolactam, 10.8 mol % 6ACA(M) and 18.7 mol % oligomers. No N-methyl caprolactam was detected in this mixture.

In two consecutive semicontinuous distillations, first, water was removed from the product stream and secondly, 2164 gr caprolactam (19.15 mol) was recovered from the product stream. The residue of the second distillation amounted to 1205 gr and according to the mass balance should contain a total of 10.13 mol of ε-caprolactam and ε-caprolactam precursors. The caprolactam yield in the first pass through the cyclization reactor was thus 65.4 mol %.

EXAMPLE V

A liquid stream (approximately 550 gr/hr) consisting of 31 gr/hr methanol, 25 gr/hr ammonia, 330 gr/hr $H_2O$ and 164 gr/hr products of which 14.2 mol % 6ACA, 39.9 mol % 6ACAM, 33.9% CAP and 12.0 mol % oligomers was continuously fed to a steamstripper column as described in Example III. Also 350 gr/hr $H_2O$ is fed to the steamstripper column (bottom temperature is maintained at approximately 100° C.). The remaining aqueous bottom stream having a rate of 742 gr/hr contained a total of 22.1 wt. % of ε-caprolactam and ε-caprolactam precursors (1.33 mol/hr).

This mixture was continuously fed to a plug flow cyclization reactor as in Example II. Also, 85 gr/hr (approximately 0.715 mol/hr) of a recycle distillation residue (see below) and 314 gr/hr $H_2O$ were fed to the cyclization reactor. Thus, overall 1141 gr/hr product mixture (21.8 wt. % products) was fed to the cyclization reactor (249 gr/hr ε-caprolactam and ε-caprolactam precursors and 892 gr/hr $H_2O$).

The cyclization was carried out at 300° C., 10 MPa and at a residence time of approximately 30 minutes. After cooling and depressurizing, the effluent of the cyclization reactor was analyzed. The mixture consisted of 70.5 mol % ε-caprolactam, 10.8 mol % 6ACA(M) and 18.7 mol % oligomers.

This cyclization mixture was continuously fed to two consecutive vacuum distillation columns. In the first column, the solvent ($H_2O$) was removed. From the second column, ε-caprolactam was recovered at a rate of 150 gr/hr (1.33 mol/hr).

The distillation residue obtained as the bottom stream in the second distillation (containing approximately a total of 0.715 mol/hr ε-caprolactam and ε-caprolactam precursors) was continuously recycled to the cyclization reactor (see above) at a rate of 85 gr/hr.

Thus, virtually a 100% caprolactam yield could be obtained in a continuous reductive amination and cyclization process using a steamstripper to remove methanol before the cyclization and by recycling of the distillation residue after recovering part of the ε-caprolactam.

The above results were obtained 3 hours after the continuous process stabilized.

Comparative Example A

The starting mixture of Example II was continuously fed to the cyclization reactor at a rate of 500 gr/hr and at a temperature of 300° C. without performing the steam stripping. The cyclization was carried out in a plugflow reactor (almost no backmixing) at a constant temperature of 300° C. (maintained with the use of an oil bath), a pressure of 10 MPa and at a residence time of 30 minutes. The effluent leaving the cyclization reactor was cooled down and depressurized to ambient conditions. The average composition of all the products present in the liquid aqueous stream amounted to 65.9 mol % CAP, 5.1 mol % of N-methyl caprolactam plus 6-N-Me ACA plus 6-N-Me ACAM, 10.8 mol % 6ACA(M) and 18.2 mol % oligomers.

By vacuum distillation, $H_2O$, $NH_3$ and methanol were semicontinuously removed from this liquid aqueous mixture. From the bottom stream of the first distillation 2515 gr ε-caprolactam (22.26 mol) and 234 gr N-methyl caprolactam plus 6-N-Me ACA plus 6-N-Me ACAM (1.84 mol) were recovered as top stream product by a second vacuum distillation. In the second distillation, 1464 gr residue (bottom product) was obtained, which according to the mass-balance contained 12.3 mol equivalent monomeric products. Analysis of the residue showed that CAP, 6ACA, 6ACAM and oligomers were present.

While the invention has been described in detail and with reference to specific embodiments thereof, it will be apparent to those of ordinary skill in the art that various changes and modifications can be made therein without departing from the spirit and scope thereof.

We claim:

1. A process for the preparation of ε-caprolactam starting from a liquid aqueous mixture containing a $C_1$–$C_6$ alcohol and 6-aminocaproic acid by cyclization of 6-aminocaproic acid in the aqueous mixture at an elevated temperature, wherein the alcohol is separated from the aqueous starting mixture before performing the cyclization so that the concentration of alcohol in the aqueous mixture during the cyclization is less than 1%;

wherein said aqueous starting mixture is obtained: (i) by reductive amination of 5-formylvaleric acid or 5-formylvalerate ester, or (ii) by reduction of 5-cyanovaleric acid or 5-cyanovalerate ester; and the aqueous starting mixture is obtained by contacting $C_1$–$C_6$ alkyl 5-formylvalerate with ammonia and hydrogen in the presence of a hydrogenation catalyst in a water solvent.

2. A process according to claim 1, characterized in that the catalyst comprises ruthenium.

3. A process according to any one of claim 1 or 2, characterized in that methyl 5-formylvalerate is used.

* * * * *